United States Patent
Li et al.

(10) Patent No.: US 11,293,878 B2
(45) Date of Patent: Apr. 5, 2022

(54) FULL-AUTOMATIC ROCK SPECIMEN IMAGE ACQUISITION DEVICE AND METHOD

(71) Applicant: SHANDONG UNIVERSITY, Shandong (CN)

(72) Inventors: Shucai Li, Jinan (CN); Zhenhao Xu, Jinan (CN); Heng Shi, Jinan (CN); Xiaoqi Chen, Jinan (CN); Tengfei Yu, Jinan (CN); Huihui Xie, Jinan (CN); Xin Huang, Jinan (CN); Yuchao Du, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 16/958,017

(22) PCT Filed: Apr. 26, 2019

(86) PCT No.: PCT/CN2019/084656
§ 371 (c)(1),
(2) Date: Jun. 25, 2020

(87) PCT Pub. No.: WO2020/199291
PCT Pub. Date: Oct. 8, 2020

(65) Prior Publication Data
US 2021/0255114 A1    Aug. 19, 2021

(30) Foreign Application Priority Data

Apr. 4, 2019   (CN) .......................... 201910272839.3

(51) Int. Cl.
*G01N 33/24* (2006.01)
*G01N 21/01* (2006.01)
(Continued)

(52) U.S. Cl.
CPC ......... *G01N 21/8901* (2013.01); *G01N 21/01* (2013.01); *G01N 21/84* (2013.01);
(Continued)

(58) Field of Classification Search
CPC .... G01N 21/8901; G01N 21/84; G01N 21/01; G01N 33/24; G01N 2021/0112; G01N 2021/0187; G06K 9/6267
See application file for complete search history.

(56) References Cited

U.S. PATENT DOCUMENTS 4,475,965 A * 10/1984 York ..................... C06B 31/285
149/112

FOREIGN PATENT DOCUMENTS

| CN | 102221550 A | 10/2011 |
| CN | 103033170 A | 4/2013 |

(Continued)

OTHER PUBLICATIONS

Dec. 27, 2019 Search Report issued in International Patent Application No. PCT/CN2019/084656.
(Continued)

*Primary Examiner* — Mark R Gaworecki
(74) *Attorney, Agent, or Firm* — Oliff PLC

(57) ABSTRACT

A full-automatic rock specimen image acquisition device and method, the device includes a central controller and a lighting system, a rock mass attitude control system, a dust system and an image acquisition system connected to the central controller respectively; the lighting system includes a lighting chamber and light sources with adjustable light intensities, and the light sources with adjustable light intensities are uniformly arranged in the lighting chamber; the rock mass attitude control system includes a rotating stage disposed in the lighting chamber for carrying the rock, a rock holder disposed on the stage, and a rotating gripper (Continued)

Fig. 5 disposed above the stage for turning over the rock; and the dust system is connected to the lighting chamber, and can diffuse the dust into the lighting chamber through an air compressor and control the dust concentration in the lighting chamber through an electrostatic precipitator.

9 Claims, 4 Drawing Sheets

(51) Int. Cl.
*G01N 21/89* (2006.01)
*G01N 21/84* (2006.01)
*G06K 9/62* (2006.01)
(52) U.S. Cl.
CPC ............ *G01N 33/24* (2013.01); *G06K 9/6267* (2013.01); *G01N 2021/0112* (2013.01); *G01N 2021/0187* (2013.01)

(56) References Cited

FOREIGN PATENT DOCUMENTS

| | | |
|---|---|---|
| CN | 104895564 A | 9/2015 |
| CN | 106205349 A | 12/2016 |
| CN | 109186480 A | 1/2019 |
| KR | 101870170 B1 | 6/2018 |

OTHER PUBLICATIONS

Dec. 27, 2019 Written Opinion of the International Searching Authority issued in International Patent Application No. PCT/CN2019/084656.

\* cited by examiner

FULL-AUTOMATIC ROCK SPECIMEN IMAGE ACQUISITION DEVICE AND METHOD

FIELD OF THE INVENTION

The present invention relates to the technical field of rock image acquisition, in particular to a full-automatic rock specimen image acquisition device and method.

BACKGROUND OF THE INVENTION

The identification of stratum lithology is of great significance, especially for the selection of a construction scheme, determination of construction parameters, project safety and project revenue. With the development of computer technology, deep learning algorithms have shown superiority in object identification, intelligent classification and the like; it has the advantages of high accuracy, fast identification and the like, and therefore, has been gradually applied in the field of engineering, and researchers have started using deep learning technologies for intelligent identification of rocks.

However, the inventors found that some challenges gradually emerged when expanding into the field of intelligent identification of rocks, such as light and dust factors during the project construction. Tunneling, slag loading and transportation, boring and rock drilling, blasting excavation, concrete spraying, etc. will generate a lot of dust. These dusts are suspended in the air, generating lots of pattern noises, which affects the quality of the on-site image acquisition and the preservation of rock color, texture and shape features.

In addition, the construction site has complex conditions and often has multiple lighting facilities. Without prior appropriate organization, these lighting facilities will affect the light intensity of a region to be shot. Sometimes the construction relies on natural light, but the lighting conditions in the same region at different time are obviously different, and the lighting conditions cannot be consistent in space and time under the effects of weather conditions such as sunny and cloudy days. Light intensity has a non-negligible impact on the use of images to preserve color, texture and shape features. For example, the development of cracks in rocks can be clearly observed from images shot when the light is sufficient, but when the light is insufficient, the contrast between the cracks and surrounding minerals is not obvious, causing that the features such as crack orientation and width cannot be accurately identified.

The successful application of deep learning technologies is inseparable from the accumulation of mass data. However, the original rock images cannot meet the needs of deep learning technologies for data volume in terms of quality or quantity. Moreover, in actual projects, the construction environments are complex, and the phenomena of dust pollution, uneven light intensity and the like often occur, which will cause huge problems for rock imaging, and pose great challenges to intelligent identification of lithology using deep learning technologies.

SUMMARY OF THE INVENTION

In order to solve the above problems, the present invention proposes a full-automatic rock specimen image acquisition device and method, which solves the problems of small amount of existing rock images acquired, varying qualities of images, little consideration of the environmental factors (such as project lighting and dust environment), low acquisition efficiency, etc.

In order to achieve the above objectives, the present invention adopts the following technical solution:

In some embodiments, the following technical solution is adopted:

A full-automatic rock specimen image acquisition device includes a central controller and a lighting system, a rock mass attitude control system, a dust system and an image acquisition system connected to the central controller respectively.

The lighting system includes a lighting chamber and light sources with adjustable light intensities, and the light sources with adjustable light intensities are uniformly arranged in the lighting chamber; the rock mass attitude control system includes a rotating stage disposed in the lighting chamber for carrying the rock, a rock holder disposed on the stage, and a rotating gripper disposed above the stage for turning over the rock; the dust system is connected to the lighting chamber, and the dust system can diffuse the dust into the lighting chamber through an air compressor and control the dust concentration in the lighting chamber through an electrostatic precipitator; and the image acquisition system includes a camera device for acquiring images of the rock.

The lighting system can provide light sources with adjustable light intensities, and the dust system can generate a dust environment with a set concentration, thereby providing different shooting environments for image acquisition of a rock specimen. The rock mass attitude control system can control the rock to rotate 360° within a horizontal plane and a vertical plane, so as to acquire rock images from multiple angles and directions.

In some other embodiments, the following technical solution is adopted:

A full-automatic rock specimen image acquisition method includes:

Providing the dust with a set concentration to the lighting chamber under the set light intensity, and detecting in real time whether the dust concentration meets the set requirement;

controlling a rock specimen to rotate in the horizontal direction, and shooting images once each time the specimen rotates a set angle;

controlling the rock specimen to turn over in the vertical direction, and shooting images once each time the specimen turns over a set angle;

adjusting the light intensity and repeating the image acquisition process mentioned above; and recovering the dust after the image acquisition is completed.

Further, the dust in the dust buffer chamber is diffused to the lighting chamber under the effect of diffusion, and whether the dust concentration in the lighting chamber meets the set requirement is detected in real time; when the dust concentration is higher than the set requirement, the electrostatic precipitator is controlled to remove dust; and when the dust concentration is lower than the set requirement, the air compressor is controlled to add dust.

Compared with the prior art, the beneficial effects of the present invention are:

Multi-angle automatic acquisition of rock specimen images can be achieved by means of rotation angle control and turnover control on the rock specimen, thus providing a data basis for deep learning technologies of rock images.

Through the adjustment of light intensity, different lighting environments can be provided for image acquisition; and through the adjustment of dust concentration, different dust concentration environments can be provided for image acquisition.

BRIEF DESCRIPTION OF THE DRAWINGS

The accompanying drawings constituting a part of the present application are intended to provide a further understanding of the present application, and the illustrative embodiments of the present application and the descriptions thereof are intended to interpret the present application and do not constitute improper limitations to the present application.

In which: 1-1 light source, 1-2 lighting chamber, 2-1 rotating stage, 2-2 rotating gripper, 3 dust system, 4 image acquisition system, 5 central controller, 6 dimming controller, 7 light source, 8 lighting sensor, 9 rock mass holder, 10 stage rotation drive, 11 stage rotation controller;

9-1 spring, 9-2 clamping block, 9-3 slide rail, 9-4 first slider, 9-5 connecting rod, 9-6 connecting block, 9-7 push tube, 9-8 push tube drive controller, 9-9 column, 9-10 push tube drive;

12 vertical movement drive controller, 13 vertical movement drive, 14 base, 15 connecting rod, 16 horizontal beam, 17 horizontal stretch drive controller, 18 horizontal stretch drive, 19 connecting rod, 20 second slider, 21 spring, 22 rotation drive controller, 23 rotation drive, 24 clip, 25 vertical movement track, 26 electrostatic precipitator, 27 dust recovery chamber, 28 dust buffer chamber, 29 air compressor, 30 dust detector, 31 dust storage tank.

DETAILED DESCRIPTION OF EMBODIMENTS

It should be noted that the following detailed descriptions are exemplary and are intended to provide further descriptions of the present application. All technical and scientific terms used herein have the same meaning as commonly understood by those of ordinary skill in the technical filed to which the present application belongs, unless otherwise indicated.

It should be noted that the terms used here are merely used for describing specific embodiments, but are not intended to limit the exemplary embodiments of the present invention. As used herein, unless otherwise clearly stated in the context, singular forms are also intended to include plural forms. In addition, it should also be understood that when the terms "comprise" and/or "include" are used in the description, it indicates the presence of features, steps, operations, devices, components, and/or combinations thereof.

Embodiment 1

Figure 1:
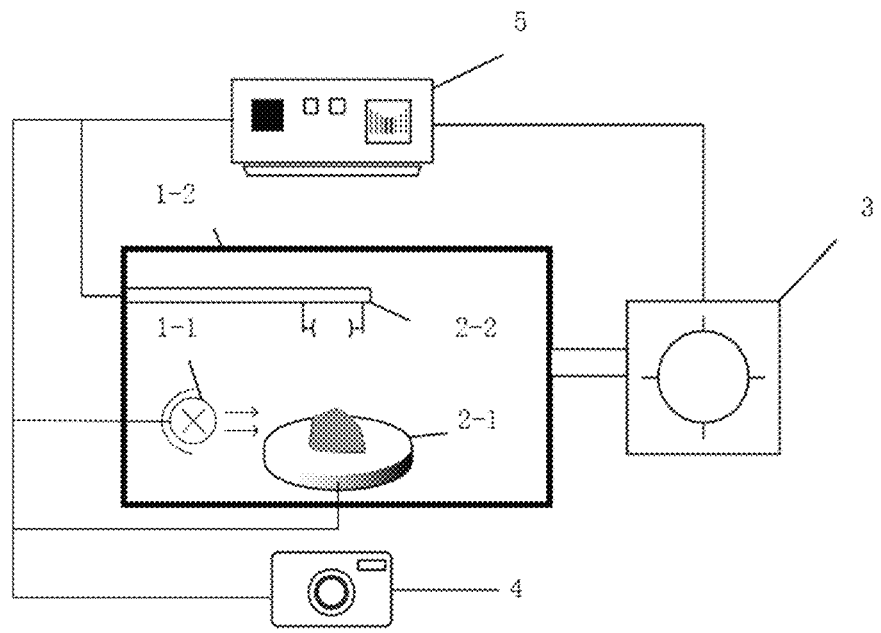
FIG. 1 is a schematic structural diagram of a full-automatic rock specimen image acquisition device in Embodiment 1.

In one or more embodiments, a full-automatic rock specimen image acquisition device is disclosed, as shown in FIG. 1, including a lighting system, a rock mass attitude control system, a dust system, an image acquisition system and a central controller.

In which, the lighting system includes a lighting chamber 1-2, and a light source 1-1 with adjustable intensity is disposed in the lighting chamber; the rock mass attitude control system includes a rotating stage 2-1 and a rotating gripper 2-2 disposed above the rotating stage 2-1; the dust system 3 is in communication with the lighting chamber 1-2, and the image acquisition system 4 is configured to acquire image information of a rock specimen on the rotating stage; and the central controller 5 is connected with the lighting system, the rock mass attitude control system, the dust system 3 and the image acquisition system 4 respectively.

Figure 2:
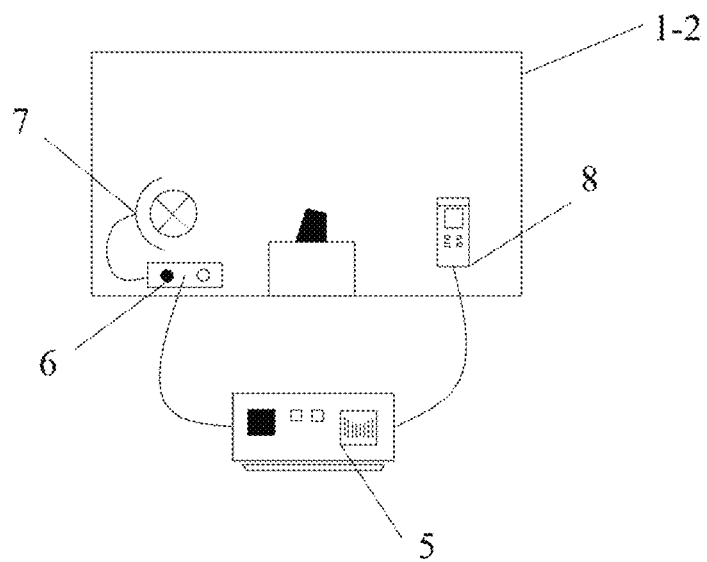
FIG. 2 is a schematic structural diagram of a lighting system in Embodiment 1.

Referring to FIG. 2, the lighting system includes a dimming controller 6, light sources 7 with adjustable light intensities, a lighting sensor 8 and a lighting chamber 1-2, wherein the light sources with adjustable light intensities are LED light strips, which are uniformly arranged on the wall of the lighting chamber to provide a uniform optical environment for shooting; the lighting chamber 1-2 is composed of soft light panels with white frosted inner walls to increase the reflection effect and ensure uniform light intensity of the lighting chamber; the central controller 5 can sense the light intensity in the lighting chamber through the lighting sensor 8 to determine whether the light intensity meets the preset requirement, and then determine whether the light intensity needs to be adjusted by the dimming controller 6; and when the light intensity is inconsistent with the preset one, the central controller 5 transmits an instruction to the dimming controller to adjust the light intensity of the lighting chamber 1-2 until the preset requirement is met. This system can adjust the light intensity in the lighting chamber to provide a good optical environment for shooting. The rock mass attitude control system is configured to control the rotation of a rock mass so as to facilitate a camera to shoot different sides of the rock mass, and includes a rotating stage 2-1, a rotating gripper 2-2 and a rock mass holder 9.

Figure 3:
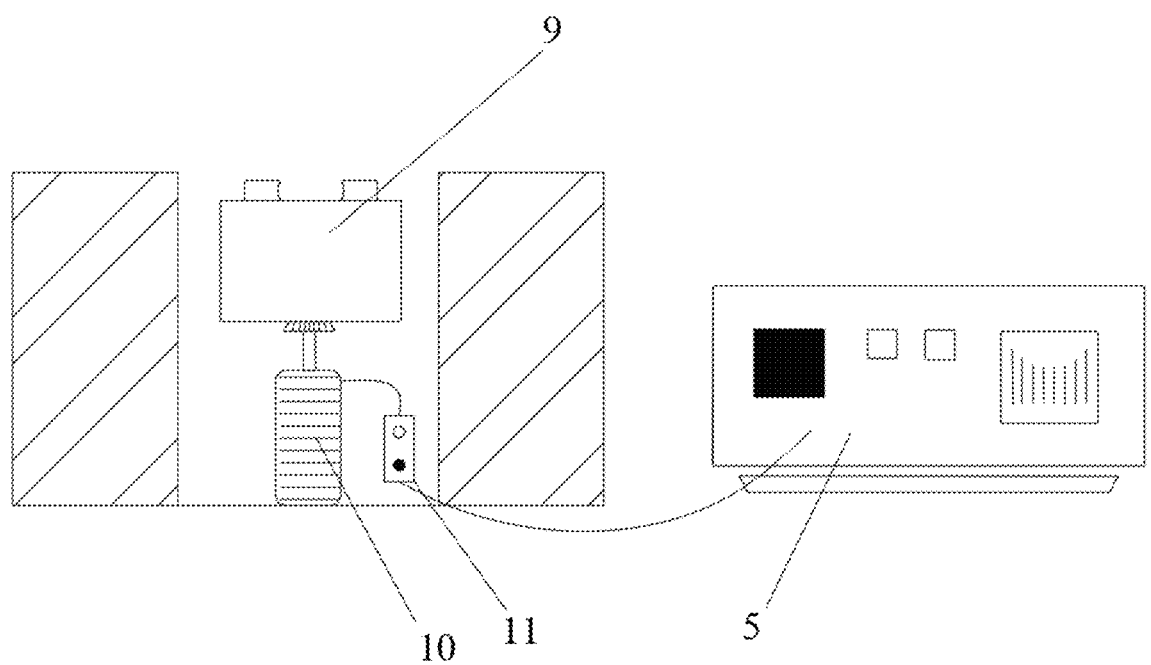
FIG. 3 is a cross-sectional view of a rotating stage in Embodiment 1.

Referring to FIG. 3, the rotating stage 2-1 includes a rock mass holder 9, a stage rotation drive motor 10 and a stage rotation controller 11. The central controller 5 controls the stage rotation drive motor 10 to rotate the rock mass holder 9 through the stage rotation controller 11 as required, thus laying a foundation for the image acquisition system to shoot the rock mass at different angles.

The rotating stage 2-1 is at the lower middle part in the lighting chamber, and the appearance of the stage looks like a black cylinder, which is in sharp contrast to rock so as to accurately distinguish the rock and the rock specimen image acquisition device; the rotation drive motor 10 is below the stage, and provides a driving force for the rotation of the stage; and the rotation controller 11 receives an instruction from the central controller 5 to control the rotation time and rotation angle of the rotation drive motor 10.

The rock mass holder is configured to hold the rock mass to prevent the movement of the rock mass, and the rock mass holder is inside the stage; and the rock mass holder is at the upper part in the lighting chamber and cooperates with the rock mass holder to turn over the rock.

Figure 4A:
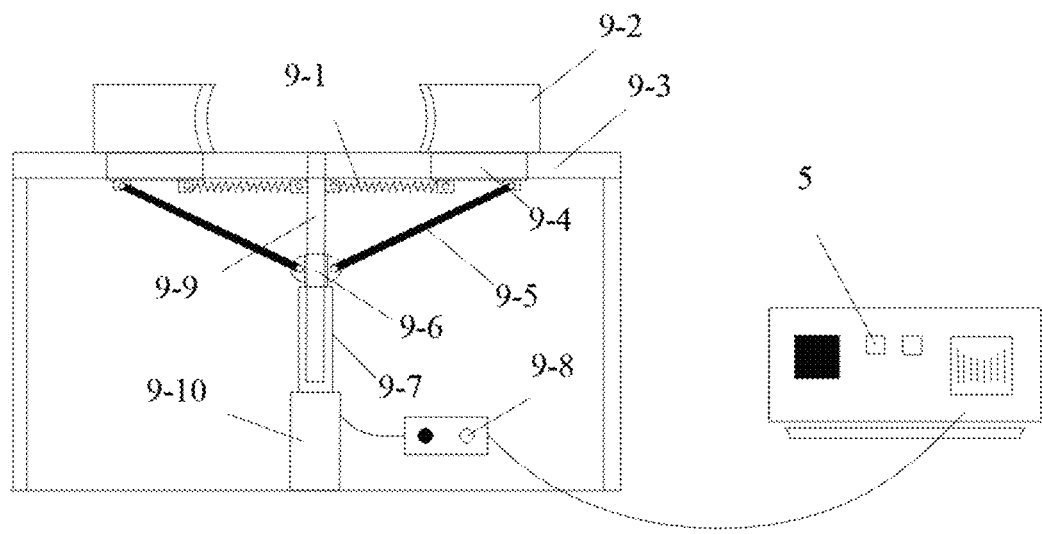
FIG. 4(a) is a schematic diagram of a rock mass holder in Embodiment 1.
Figure 4B:
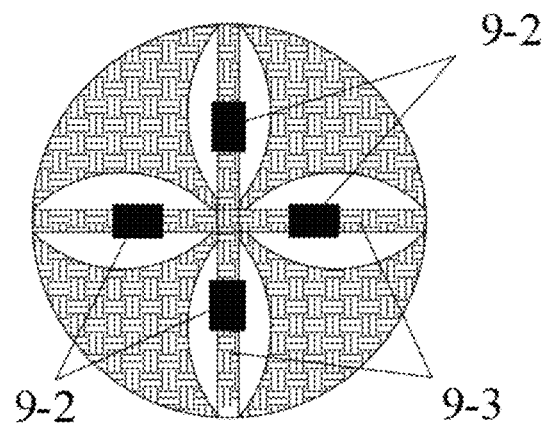
FIG. 4(b) is a top view of the rock mass holder in Embodiment 1.

Referring to FIG. 4(a) and FIG. 4(b), the structure of the rock mass holder specifically includes springs 9-1, clamping blocks 9-2, slide rails 9-3, first sliders 9-4, connecting rods 9-5, a connecting block 9-6, a push tube 9-7, a push tube drive controller 9-8, a column 9-9 and a push tube drive 9-10.

The rock mass holder has four clamping blocks, and a spring is disposed on each clamping block; each clamping block 9-2 is connected to a first slider 9-4, and the first slider 9-4 slides in a slide rail 9-3. The drive controller is connected to the central controller; each clamping block 9-2 is connected to the connecting block disposed on the column 9-9 through a connecting rod; during the operation, the push tube drive controller 9-8 controls the push tube drive 9-10 to push the push tube 9-7 upward, the push tube 9-7 pushes the connecting rods 9-5 to move, the connecting rods 9-5 drive the clamping blocks 9-2 to open outward, and the springs stretch; after the push tube drive 9-10 stops operating, the springs retract to pull the clamping blocks 9-2 to clamp the rock specimen; and the clamping blocks 9-2 have threads thereon to ensure that the clamping blocks clamp the specimen without slipping.

Figure 5:
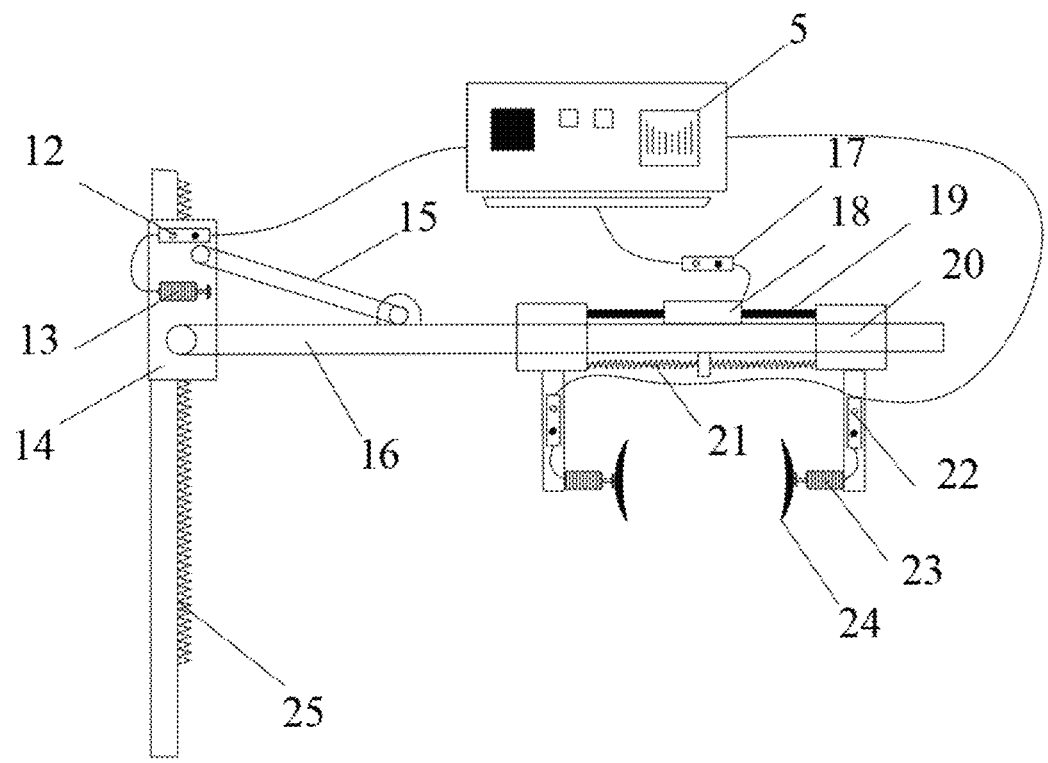
FIG. 5 is a schematic diagram of a rotating gripper in Embodiment 1.

Referring to FIG. 5, the rotating gripper can grasp the specimen to rotate within a vertical plane. The rotating gripper is configured to turn over the rock mass within the vertical plane, thus laying a foundation for 360-degree shooting of rock. The rotating gripper includes a vertical movement drive controller 12, a vertical movement drive 13, a base 14, a connecting rod 15, a horizontal beam 16, a horizontal stretch drive controller 17, a horizontal stretch drive 18, a connecting rod 19, sliders 20, a spring 21, a rotation drive controller 22, a rotation drive 23, clips 24, and a vertical movement track 25.

The vertical movement drive controller 12, the horizontal stretch drive controller 17 and the rotation drive controller 22 are respectively connected to the central controller 5, and receive corresponding control.

The central controller 5 controls the rotation drive 23 through the rotation drive controller 22 to control the rotation of the clips 24. The clips 24 are fixed on the second sliders 23, and the two clips 24 can move relative to each other along the horizontal beam 16 in the following manner: the central controller 5 controls the horizontal stretch drive 18 through the horizontal stretch drive controller 17 to stretch the connecting rod 19, and the connecting rod 19 drives the two second sliders 23 to move away from each other, thereby opening the two clips; the two second sliders 23 are respectively connected to a fixed block between the two clips 24 through the spring; and after the horizontal stretch drive controller 17 stops operating, the two second sliders 23 retract under the tension of the spring, and then drive the two clips 24 to approach each other, thus clamping the rock.

The horizontal beam 16 is fixed on the base 14, and the connecting rod 15 is configured to provide a pulling force, so that the horizontal beam can be stably fixed on the base 14. The base 14 can move up and down along the vertical movement track 25. The central controller 5 controls the vertical movement drive 13 through the vertical movement drive controller 12, so that the base 14 can move up and down along the vertical movement track 25.

Figure 6:
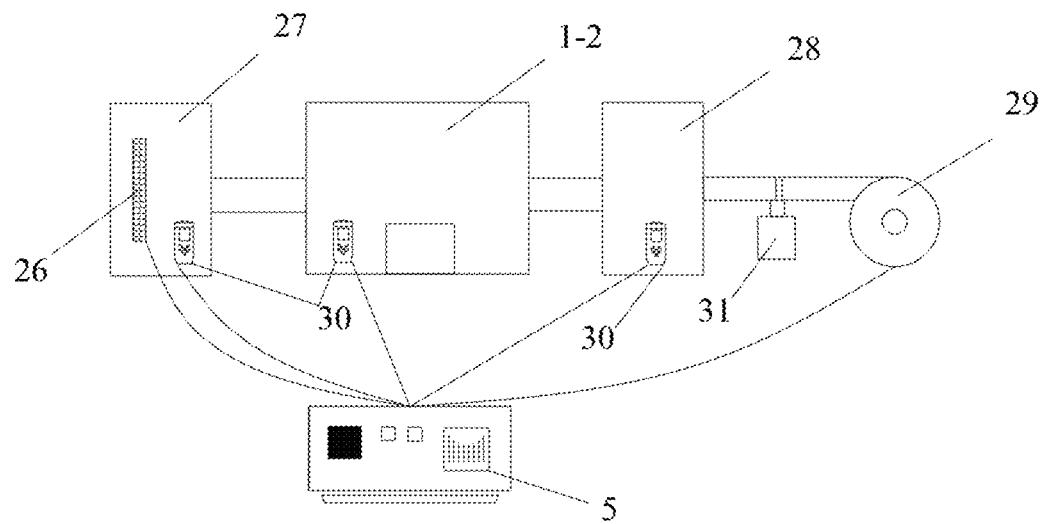
FIG. 6 is a schematic diagram of a dust system in Embodiment 1.

Referring to FIG. 6, the dust system is configured to generate a dust environment and to recover dust, including an electrostatic precipitator 26, a dust recovery chamber 27, a dust buffer chamber 28, an air compressor 29, dust detectors 30, and a dust storage tank 31; the dust storage tank 31 is configured to store the prepared dust; the air compressor 29 is configured to push the dust in the dust storage tank 31 to be diffused to the dust buffer chamber 27, the lighting chamber 1-2 and the dust recovery chamber 27; and the electrostatic precipitator 26, the dust detectors 30 and the air compressor 29 are all connected to the central controller 5 and receive the corresponding control.

A dust detector is disposed inside the dust buffer chamber and can detect the dust density in real time, the dust buffer chamber is connected to the lighting chamber, and dust can be slowly diffused to the lighting chamber through a connection port and then to the dust recovery chamber. A dust detector is disposed in the lighting chamber, and can detect the dust density in the lighting chamber in real time.

An electrostatic precipitator 26 and a dust detector are disposed in the dust recovery chamber to reduce dust concentration, recover dust and detect dust concentration. The electrostatic precipitator 26 is connected to the central controller 5 and receives the corresponding control.

The central controller 5 determines whether the dust environment of the lighting chamber meets the preset requirement through the three dust detectors, and the central controller 5 controls, when the dust environment does not meet the preset requirement, the air compressor and the electrostatic precipitator 26 in the dust recovery chamber to control the dust concentration. The dust buffer chamber is configured to provide a dust buffer space so as to ensure that the dust in the lighting chamber is uniformly distributed.

The image acquisition system includes a camera 4 and a shooting controller. The camera 4 is connected to the central controller through the shooting controller to control the shooting time of the camera. The camera 4 is disposed outside the lighting chamber, and a circular transparent dust-proof glass is inlaid on the place of the outer wall of the lighting chamber corresponding to the camera 4 to facilitate shooting.

Embodiment 2

In one or more embodiments, a full-automatic rock specimen image acquisition method is disclosed, including the following steps:

A. The central controller 5 controls the operation of the air compressor 29 to generate airflow, so as to discharge the dust in the dust storage tank 31 into the dust buffer chamber 28.

B. The dust in the dust buffer chamber 28 is diffused to the lighting chamber 1-2 under the effect of diffusion, and the dust detector 30 in the lighting chamber 1-2 transmits real-time detection data to the central controller 5 to detect whether the dust environment meets the preset requirement; when the dust concentration is higher than the preset requirement, the central controller 5 controls the electrostatic precipitator 26 and the air compressor 29 to reduce the dust concentration; when the dust concentration is lower than the preset requirement, the central controller 5 instructs the electrostatic precipitator 26 to stop operating and the air compressor 29 to accelerate the generation of airflow to increase the dust concentration, until the dust environment meets the requirement.

C. The central controller 5 controls the camera 4 to shoot images, and each time of shooting one image the central controller 5 instructs the stage rotation controller 11 to control the rock mass holder 9 to rotate a certain angle until rotating a full circle.

D. The central controller 5 transmits an instruction to the push tube drive controller 9-8, the push tube drive 9-10 is controlled to operate, the push tube 9-7 and the connecting block 9-6 are pushed to move up, and the connecting rods 9-5 push the clamping blocks 9-2 to overcome the tension of the spring 9-1 and to move outward along a chute 9-4 to release the specimen.

E. The central controller 5 transmits an instruction to the horizontal stretch drive controller 17, so that the horizontal stretch drive 18 operates to overcome the resistance of the spring 21 and to open the sliders 20; the central controller 5 transmits an instruction to the vertical movement drive controller 12 to control the operation of the vertical movement drive 13, so that the supporting beam 16 descends to a specified position; the central controller 5 transmits an instruction to the horizontal stretch drive controller 17 for the rock mass, so that the horizontal stretch drive 18 releases the pushing effect on the connecting rod 18, the sliders 20 move toward each other under the action of the spring 21, and the clips 24 finally clamp the specimen; the central controller 5 transmits an instruction to the rotation drive controller 22 to control the rotation of the rotation drive 23 within the vertical plane.

F. The central controller 5 transmits an instruction to the push tube drive controller 9-8, the push tube drive 9-10 is controlled to operate, the push tube 9-7 and the connecting block 9-6 are pulled to move down, and the clamping blocks move inward along chutes under the tension of the springs 9-1 to clamp the specimen.

G. The central controller 5 transmits an instruction to the horizontal stretch drive controller 17, so that the horizontal stretch drive 18 operates to overcome the resistance of the spring and to open the sliders to release the specimen; the central controller 5 transmits an instruction to the vertical movement drive controller 12 to control the operation of the vertical movement drive 13, so that the supporting beam 16 ascends to a specified position.

H. Step C is repeated to shoot the rock mass until the rock mass is rotated one circle within the vertical plane.

I. After the rock mass is shot at all preset angles, the central controller 5 instructs the air compressor 29 to stop operating, instructs the electrostatic precipitator 26 to recover dust, and continuously monitors the data transmitted by the dust detectors until no dust is in the lighting chamber 1-2, the dust buffer chamber 28 and the dust recovery chamber 27.

Although the specific embodiments of the present invention are described above in combination with the accompanying drawings, the protection scope of the present invention is not limited thereto. It should be understood by those skilled in the art that various modifications or variations could be made by those skilled in the art based on the technical solution of the present invention without any creative effort, and these modifications or variations shall fall into the protection scope of the present invention.

The invention claimed is:

1. A full-automatic rock specimen image acquisition device comprising:
a central controller and a lighting system, a rock mass attitude control system, a dust system and an image acquisition system connected to the central controller, wherein
the lighting system comprises a lighting chamber and light sources with adjustable light intensities, and the light sources with adjustable light intensities are uniformly arranged in the lighting chamber; the rock mass attitude control system comprises a rotating stage disposed in the lighting chamber for carrying a rock, a rock holder disposed on the stage, and a rotating gripper disposed above the stage for turning over the rock; the dust system comprises a dust storage tank, an air compressor, a dust buffer chamber, and a dust recovery chamber, the dust storage tank is in communication with the dust buffer chamber through the air compressor, the dust buffer chamber is in communication with the lighting chamber, the air compressor diffuses dust into the lighting chamber, the lighting chamber is in communication with the dust recovery chamber, an electrostatic precipitator is disposed in the dust recovery chamber, and the electrostatic precipitator controls dust concentration in the lighting chamber; and the image acquisition system comprises a camera device for acquiring images of the rock.

2. The full-automatic rock specimen image acquisition device according to claim 1, wherein the lighting system further comprises a dimming controller and a lighting sensor, the dimming controller is connected to the light sources with adjustable light intensities, the lighting sensor detects light intensity information in the lighting chamber and feeds back the information to the central controller, and the central controller determines whether a light intensity is consistent with a preset value, the central controller controls, if the light intensity is not consistent, the dimming controller to adjust the light intensity until the light intensity in the lighting chamber meets the preset value.

3. The full-automatic rock specimen image acquisition device according to claim 1, wherein the rotating stage is connected to a rotation drive motor, the rotation drive motor rotates under the control of a rotation controller so as to drive the stage to rotate, and the rotation controller receives instructions from the central controller to control a rotation time and a rotation angle of the rotation drive motor.

4. The full-automatic rock specimen image acquisition device according to claim 1, wherein the rock holder comprises at least one pair of a retractable first clamping block and a retractable second clamping block disposed on the stage, and the first clamping block and the second clamping block are symmetrically arranged in opposite directions with the center of the stage as a center point; a slide rail is disposed inside the stage along the opposite directions of the first and second clamping blocks, the first clamping block is connected to a first slider, the second clamping block is connected to a second slider, the first and second sliders slide in the slide rail through a driving device so as to drive the corresponding first and second clamping blocks to move, and the first slider and the second slider are respectively connected to a column through springs;
the driving device drives the first and second clamping blocks to move in the opposite directions, the driving device stops operating after the rock is placed in, and the first and second clamping blocks retract under an elastic force of the springs to clamp the rock.

5. The full-automatic rock specimen image acquisition device according to claim 4, wherein the driving device comprises a sliding sleeve, a first connecting rod, a second connecting rod, a push tube, and a push tube drive; a first end of each of the first connecting rod and the second connecting rod are respectively fixed to the sliding sleeve, a second end of the first connecting rod is connected to the first slider, and a second end of the second connecting rod is connected to the second slider;
the sliding sleeve is sleeved on the column, the push tube drive drives the push tube to move up, and the push tube pushes the sliding sleeve to slide upward along the column, thereby driving the first and second sliders to move in the opposite directions through the first connecting rod and the second connecting rod respectively.

6. The full-automatic rock specimen image acquisition device according to claim 1, wherein the rotating gripper comprises a base capable of moving up and down in a vertical direction, a horizontal beam is connected to the base, and two clamping devices are oppositely arranged on the horizontal beam; and the two clamping devices can move oppositely along the horizontal beam under a drive of a driving device, so that the two clamping devices approach and separate.

7. The full-automatic rock specimen image acquisition device according to claim 1, wherein a dust detector is disposed in the lighting chamber, the dust buffer chamber and the dust recovery chamber respectively to monitor dust densities in the chambers in real time; and the central controller determines whether the dust concentration in the lighting chamber meets a set requirement according to the monitored dust density, the central controller controls the electrostatic precipitator to operate if the dust concentration is too high, and controls the air compressor to operate if the dust concentration is too low.

8. A full-automatic rock specimen image acquisition method, comprising:
    a step (1): providing dust with a set concentration to a lighting chamber under a set light intensity, and detecting in real time whether dust concentration meets a set requirement;
    a step (2): controlling a rock specimen to rotate in a horizontal direction, and shooting images once each time the rock specimen rotates a first set angle;
    a step (3): controlling the rock specimen to turn over in a vertical direction, and shooting images once each time the rock specimen turns over a second set angle;
    a step (4): adjusting the set light intensity and repeating the step (2) and the step (3); and
    a step (5): recovering the dust after the step (4) is completed.

9. The full-automatic rock specimen image acquisition method according to claim 8, wherein the dust is disposed in a dust buffer chamber and is diffused to the lighting chamber under the effect of diffusion, and whether the dust concentration in the lighting chamber meets the set requirement is detected in real time; when the dust concentration is higher than the set requirement, an electrostatic precipitator is controlled to remove the dust; and when the dust concentration is lower than the set requirement, an air compressor is controlled to add the dust.

\* \* \* \* \*